US00PP36338P2

(12) United States Plant Patent
Kordes

(10) Patent No.: US PP36,338 P2
(45) Date of Patent: Dec. 31, 2024

(54) CLIMBING ROSE PLANT NAMED 'KORsilu15'

(50) Latin Name: *Rosa hybrida*
Varietal Denomination: KORsilu15

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/667,191

(22) Filed: May 17, 2024

(51) Int. Cl.
*A01H 5/02* (2018.01)
*A01H 6/74* (2018.01)

(52) U.S. Cl.
USPC ..... Plt./111
CPC ..... *A01H 6/749* (2018.05)

(58) Field of Classification Search
USPC ..... Plt./111
CPC ..... A01H 5/0222
See application file for complete search history.

(56) References Cited

U.S. PATENT DOCUMENTS

PP23,774 P3 7/2013 Meilland

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of climbing rose plant, referred to by its cultivar name, 'KORsilu15', is described. The new variety forms in abundance on a substantially continuous basis yellow-colored blossoms. The vegetation is vigorous, and the growth habit is very bushy and climbing. Semi-glossy, medium green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORsilu15'.

STATEMENT REGARDING PRIOR DISCLOSURES BY THE INVENTOR

The first offer for sale of the new variety was June 2023, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of climbing rose plant of the present invention was created by controlled breeding in May 2015 in Offenseth-Sparrieshoop, Germany by artificial pollination wherein two parents were crossed which previously had been studied in the hope that they would contribute the desired characteristics. The female parent (i.e., the seed parent) of the new variety was the 'LENsena' variety (not patented). The male parent (i.e., the pollen parent) of the new variety was an unnamed breeder seedling (not patented).

The parentage of the new variety can be summarized as follows:

'LENsena' x unnamed breeder seedling

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of climbing rose plant of the present invention possesses the following combination of characteristics:

(a) forms yellow-colored blossoms,
(b) exhibits a very bushy and climbing growth habit, and
(c) provides ornamental semi-glossy, medium green foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a more upright and climbing growth habit and smaller clusters of flowers compared to the 'LENsena' variety (i.e., the seed parent). Additionally, the new variety displays a smaller flower size and a higher petal count compared to flowers of the unnamed breeder seedling parent (i.e., the pollen parent). Moreover, the new variety can be readily distinguished from non-parental related similar varieties. For example, the new variety displays a higher petal count, smaller flower diameter, and smaller petal size compared to the 'Meilaclost' variety (U.S. Plant Pat. No. 23,774).

The new variety has been named the 'KORsilu15' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field in Ellerhoop, Germany in July 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical features. The description is based on a two-year-old specimen of the new variety, observed during August, while growing on its own roots in a field in Cochranville, Pennsylvania.

Botanical classification: *Rosa hybrida* cultivar 'KORsilu15'.

Commercial classification: Climbing Rose.

Plant:

*Habit*.—Bushy and upright.

*Height*.—Approximately 90.0 cm to 105.0 cm on average from the top of the soil plane when growing in the ground.

*Width*.—Approximately 105.0 cm on average.

Branches:

*Stem color*.—Old wood: Green Group 143C. — young stems: Yellow-Green Group 144A.

*Stem texture*.—Smooth.

*Length*.—Main stems: approximately 105.0 cm on average. — secondary stems: approximately 60.0 cm on average.

*Diameter*.—Main stems: approximately 1.0 cm on average. — secondary stems: approximately 5.0 mm on average.

*Thorns*.—Amount: few to no thorns on top half of plant, moderate amount on main stems on lower half of plant. — young thorns: length is approximately 1.1 cm on average; width is approximately 1.0 cm on average at point of attachment; and color is Greyed-Yellow Group 161A. — old thorns: length is approximately 1.3 cm on average; width is approximately 1.0 cm on average at point of attachment; and color is Greyed-Orange Group 165A.

Leaflets:

*Number*.—5 and 7.

*Shape*.—Ovate; apex is acute to acuminate; and base is cuneate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 6.0 cm on average; width is approximately 3.2 cm on average. — lower leaflets: length is approximately 4.0 cm to 5.0 cm on average; width is approximately 2.5 cm to 3.0 cm on average. — 5-Leaflet leaf: length is approximately 10.5 cm on average; width is approximately 10.0 cm on average.

Foliage:

*Young foliage*.—Upper surface color: Yellow-Green Group 146A with Greyed-Red Group 178A around edges with venation of Green Group 141A. — under surface color: Yellow-Green Group 146C and Greyed-Red Group 178A with venation of Greyed-Red Group 178A and Green Group 138A.

*Old foliage*.—Upper surface color: Green Group 137A with venation of Green Group 138A. — under surface color: Yellow-Green Group 146C and Greyed-Red Group 178A with venation of Yellow-Green Group 145C.

*Petiole*.—Texture: upper surface is hispidulous; under surface is setulose. — length: approximately 1.5 cm on average. — width: approximately 1.0 mm on average. — upper surface color: Yellow-Green Group 144A. — under surface color: Yellow-Green Group 144B.

*Rachis*.—Length: approximately 2.0 cm on average. — width: approximately 1.0 mm on average. — upper surface color: Yellow-Green Group 144A. — under surface color: Yellow-Green Group 144B.

*Stipules*.—Length: approximately 2.5 cm on average. — width: approximately 5.0 mm on average. — margin: entire to erose. — upper surface color: Yellow-Green Group 146C. — lower surface color: Yellow-Green Group 146B.

Inflorescence:

*Number of flowers*.—About 70 to 115 blooms on average on a plant at once.

*Number of blossoms per stem or in a cluster*.—Typically 5 to 8 blooms per stem on average.

*Peduncle*.—Color: mainly Greyed-Orange Group 176A with some Yellow-Green Group 146A throughout. — diameter: approximately 1.0 mm on average. — length: approximately 2.0 cm on average. — surface texture: smooth.

*Sepals*.—Number: 5. — upper surface color and texture: Yellow-Green Group 144A and Greyed-Red Group 178A, covered in short pubescence. — under surface color and texture: Yellow-Green Group 144D, puberulent. — size: length is approximately 1.1 cm on average; width is approximately 4.0 mm on average. — margin: entire with extension on most sepals measuring approximately 2.0 mm in length and 1.0 mm in width on average. — shape: lanceolate. — apex: acute to aristate. — base: truncate as it joins the receptacle.

*Buds*.—Shape: ovoid. — size: length is approximately 1.1 cm on average; width is approximately 1.1 cm on average. — color (when opening): Yellow Group 9A.

*Flower*.—Form: double, cuplike. — profile: concave as it opens, and then outer petals are convex as the bloom ages and opens further. — diameter: approximately 4.0 cm on average. — height: approximately 1.0 cm on average. — duration: on the plant approximately 10 to 12 days. — petal color when first and fully opened: upper surface is Yellow Group 8B and Yellow Group 8C with no distinct basal spot; under surface is Yellow Group 8B with no distinct basal spot. — petal color at end of bloom: upper surface is Yellow Group 8C with no distinct basal spot; under surface is Yellow Group 8D with no distinct basal spot.

*Fragrance*.—Strong sweet scent.

*Petal*.—Number: 45 to 50 on average. — drop: good. — length: approximately 1.5 cm to 2.0 cm on average. — width: approximately 1.3 cm to 1.5 cm on average. — texture: smooth (both surfaces). — overall shape: broadly obovate. — margin: entire with moderate undulation. — apex shape: rounded to slightly cuspidate. — base shape: cuneate.

*Petaloids*.—Number: approximately 4 on average. — length: approximately 1.0 cm on average. — width: approximately 5.0 mm on average. — color: upper and under surfaces are Yellow Group 8B and Yellow Group 8C. — shape: lanceolate. — apex: rounded to slightly cuspidate. — base: cuneate. — margin: entire. — texture: smooth (both surfaces).

*Stamen*.—Number: approximately 32. — anthers: number is approximately 32; color is Yellow-Orange Group 22A; length is approximately 2.0 mm on average; and shape is oval. — filaments: length is approximately 5.0 mm on average and color is Yellow-Orange Group 17C.

*Pistils*.—Arrangement: separate and free. — number: approximately 26. — style: length is approximately 6.0 mm on average and color is Yellow Group 2C and Red Group 46C. — stigma: diameter is approximately 1.0 mm on average; shape is fan shaped; and color is Yellow-Orange Group 21B.

*Receptacle*.—Diameter: approximately 5.0 mm on average. — depth: approximately 5.0 mm on average. — shape: urn shaped. — color: Yellow-Green Group 144A. — surface texture: smooth.

*Pollen*.—Amount: sparse. — color: Yellow-Orange Group 20A.

*Hips/seed*.—None observed.

Development:

*Vegetation*.—Semi-glossy, medium green, vigorous and strong.

*Blossoming*.—Abundant and continuous from spring through frost; typically, in bloom outdoors from May to November in Southeastern Pennsylvania.

*Resistance to diseases*.—Very good resistance for powdery mildew (*Sphaerotheca pannosa*) and leaf spot (*Cercospora rosicola*).

*Hardiness*.—Hardy to USDA Zone 6; further hardiness testing is in progress.

The new 'KORsilu15' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of climbing rose plant named 'KORsilu15' characterized by the following combination of characteristics:

(a) forms yellow-colored blossoms, (b) exhibits a very bushy and climbing growth habit, and (c) provides ornamental semi-glossy, medium green foliage; substantially as herein shown and described.

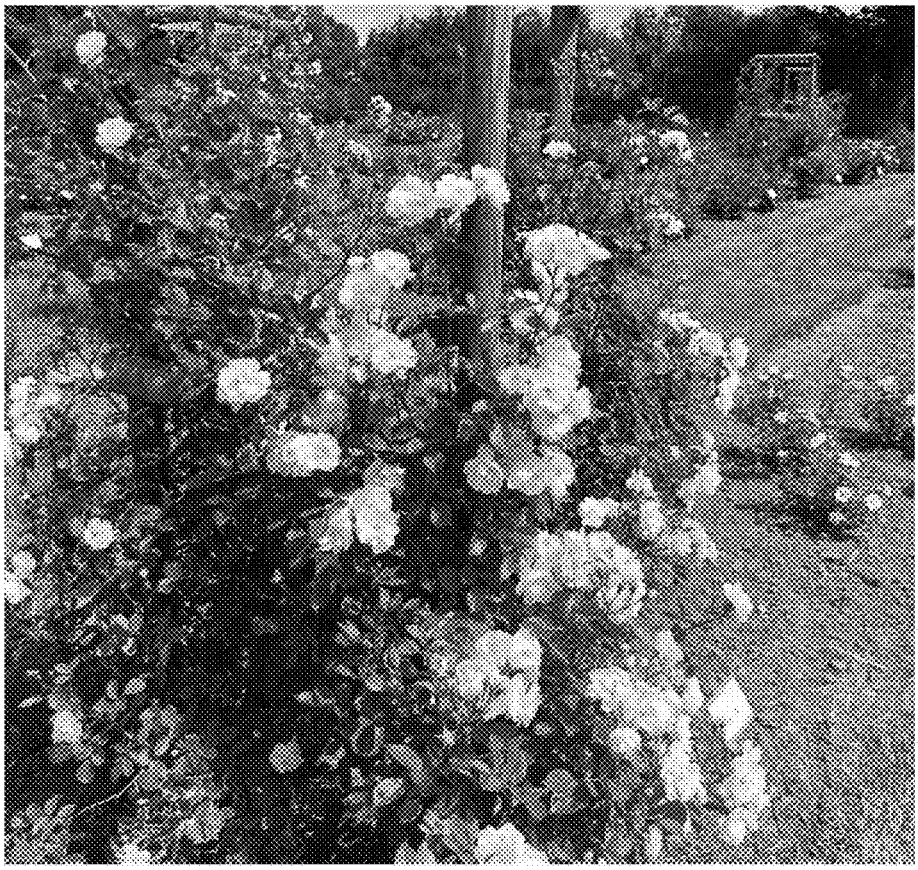

* * * * *